US00PP15808P2

(12) United States Plant Patent
Warren et al.

(10) Patent No.: US PP15,808 P2
(45) Date of Patent: Jun. 28, 2005

(54) ***CALLA* LILY PLANT NAMED 'BLACK JACK'**

(50) Latin Name: ***Zantedeschia* sp.**
Varietal Denomination: Black Jack

(75) Inventors: Andrew Geoffrey Fiennes Warren, Tauranga (NZ); Jacobus Petrus Spaans, Tauranga (NZ)

(73) Assignee: BLOOMZ Ltd., Tauranga (NZ)

( * ) Notice: Subject to any disclaimer, the term of this patent is extended or adjusted under 35 U.S.C. 154(b) by 135 days.

(21) Appl. No.: 10/766,112
(22) Filed: Jan. 27, 2004
(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Jondle & Associates P.C.

(57) ABSTRACT

A *calla* lily plant particularly distinguished by dark purple spathe and maculated leaves.

3 Drawing Sheets

Genus and species: *Zantedeschia* sp.
Variety denomination: 'Black Jack'.

BACKGROUND OF THE NEW PLANT

The present invention comprises a new and distinct cultivar of *calla* lily, botanically known as *Zantedeschia* sp, and hereinafter referred to by the cultivar name 'Black Jack'. The new cultivar is asexually reproduced from vegetative cuttings and tissue culture resulting from the cross of the female parent 'Cameo' (patent status unknown) and the male parent is an unnamed, unpatented seedling from the Bloomz breeding pool.

'Black Jack' is a product of a planned breeding program intended to create new *calla* lily plants with dark purple–black spathes.

The new cultivar was created in 2001 in Tauranga New Zealand and has been asexually reproduced repeatedly by vegetative cuttings and tissue culture in New Zealand over a 2 year period. The present invention has been found to retain its distinctive characteristics through successive propagations; and this novelty is firmly fixed. 'Black Jack' reproduces true to type through successive generations of asexual reproduction.

DESCRIPTION OF PHOTOGRAPH

This new *calla* lily plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
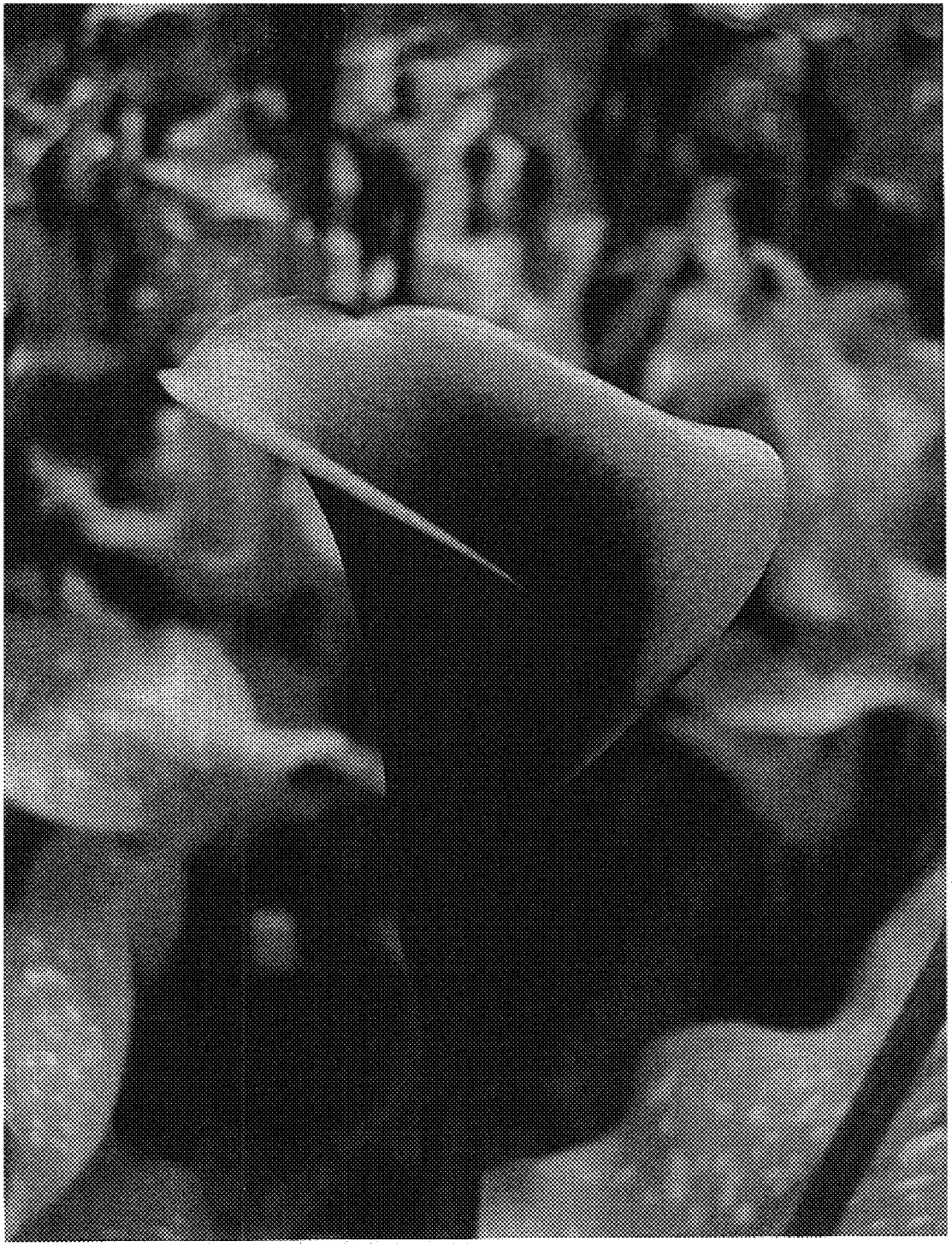
FIG. 1 shows the mature inflorescence.
Figure 2:
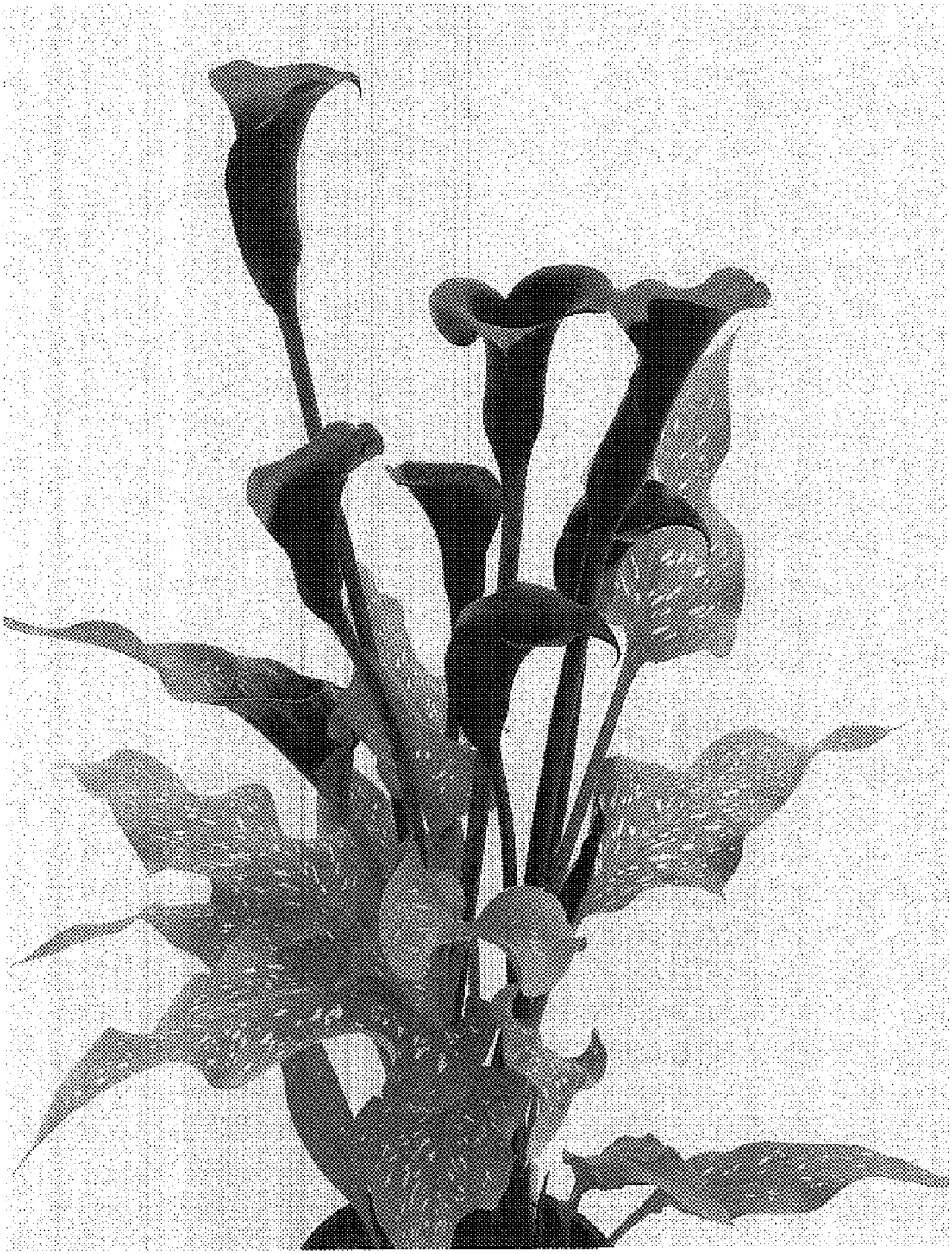
FIG. 2 shows the overall plant habit.
Figure 3:
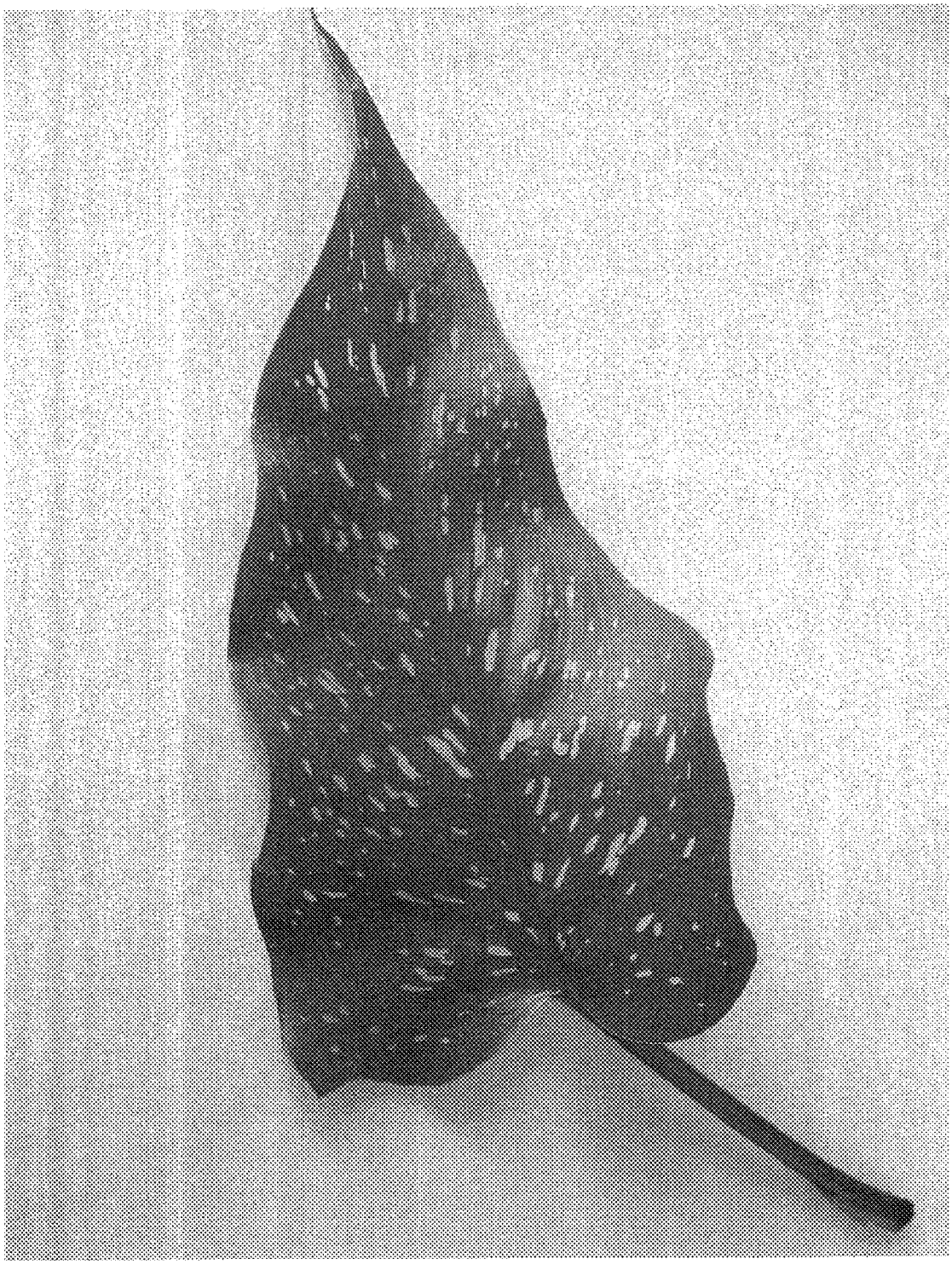
FIG. 3 shows a close-up of the leaf.

The following detailed descriptions set forth the distinctive characteristics of 'Black Jack'. The data that defines these characteristics were collected from asexual reproductions carried out in New Zealand. The plant history was taken on 2 year old plants based on a 3 cm diameter tuber under New Zealand Summer conditions. Color references are primarily to The R.H.S. Colour Chart of The Royal Horticultural Society of London (R.H.S.).

THE PLANT

Classification:
- *Botanical.*—*Zantedeschia* sp.
- *Commercial.*—*Calla* lily.
- *Variety.*—'Black Jack'.

Size:
- *Form.*—Erect.
- *Height of the leaf canopy above the soil.*—25–40 cm.
- *Height of top of inflorescence above the soil.*—30–40 cm.
- *Diameter.*—25–30 cm.
- *Number of inflorescence per tuber size.*— Tuber diameter 3 cm 2–4. Tuber diameter 4 cm 4–6. Tuber diameter 5 cm 6+.

Branches:
- *Character.*—Strong.
- *Color.*—Upper surface is green RHS 144A; lower surface is Dark Purple RHS 187B; base is white RHS 155C.
- *Average number.*—3–4.

Leaves:
- *Size.*—Width 5–10 cm; length 13–20 cm.
- *Shape.*—Ovate.
- *Color.*—Upper surface is green RHS 137B; occasionally middle section splotch is present and is about Dark purple RHS 187A–202A; lower surface is green RHS 137C.
- *Maculation* (*leaf spots*).—Medium density; white RHS 155C.
- *Apex.*—Acute to apiculate.
- *Margin.*—Moderately wavy, entire.
- *Margin color.*—Yellow-Green RHS 144A.
- *Veins.*—Pinnate.
- *Surface quality.*—Leathery.

Petiole (leaf stalk):
- *Length.*—10–15 cm.
- *Color.*—Base is Dark Purple RHS 187B; upper is green RHS 144A.

Roots:
- *Color.*—White.
- *Branching.*—Not branched, attached to the top of the tuber at the apices.
- *Disease resistance.*—No susceptibility noted to date.
- *Pest resistance.*—No susceptibility noted to date.

THE INFLORESCENCE

Spathe (flower body):

*Size.*—Length 5–7 cm; width 3–5 cm.

*Color.*—Upper surface is Dark Purple RHS 187A–202A; lower surface is Dark Purple RHS 187A.

*Veins.*—Present, black RHS 202A.

*Shape.*—Fluted, acute apex, entire wavy margin.

Spadix (reproductive organs):

*Size.*—Length 2–2.5 cm; diameter 0.4–0.7 cm.

*Color.*—Base is Dark Purple RHS 187A; Upper is Dark Purple RHS 187A.

*Position relative to spathe.*—Upright.

Peduncle (flower stem):

*Size.*—20–40 cm in length, 6–8 mm in diameter.

*Color.*—Base is Dark Purple RHS 187A; upper is Dark Purple RHS 187B.

Reproductive organs:

*Location of female organs.*—Basal position of the spadix.

*Location of male organs.*—Upper position of the spadix.

*Perianth* (*the floral envelope — calyx and corolla*).—Conspicuous.

*Stamens.*—Not visible before pollen release.

*Pistil.*—10–20 per spadix; purple RHS 186D.

Miscellaneous:

*Time to produce a finished flowering plant.*—6–10 weeks.

*Lastingness of bloom on the plant.*—2–3 weeks.

*Fragrance.*—None.

Fruit:

*Production.*—10–20 berries.

*Color.*—Predominantly dark purple RHS 187A with green RHS 143A markings.

COMPARISON WITH KNOWN CULTIVARS

When the instant plant is compared to 'Ruby Lite Red' (patent status unknown) the 'Black Jack' foliage has a medium density of maculation and the shape of the leaves is ovate towards arrow shaped. Additionally the spathe color is different than 'Ruby Lite Red'. 'Black Jack' is a miniature version of 'Hot Chocolate' (co-pending U.S. Plant patent application Ser. No. 10/382,957). When the instant plant is compared to 'Hot Chocolate' the spathe size, stem length and overall plant size are significantly and noticeably smaller.

When the instant plant is compared to the female parent, 'Cameo', 'Black Jack' has dark purple—black spathes whereas 'Cameo' has salmon-pink spathes. 'Crackerjack' is distinguished from the male parent primarily in spathe color.

I claim:

1. A new and distinct cultivar of *calla* lily plant as shown and described herein.

* * * * *

UNITED STATES PATENT AND TRADEMARK OFFICE

CERTIFICATE OF CORRECTION

PATENT NO. : PP 15,808 P2 
DATED : June 28, 2005
INVENTOR(S) : Andrew Geoffrey Fiennes Warren and Jacobus Petrus Spaans It is certified that error appears in the above-identified patent and that said Letters Patent is hereby corrected as shown below:

Column 4,
Line 20, "Crackerjack", should read -- Black Jack --.

Signed and Sealed this

Eighth Day of November, 2005

JON W. DUDAS
*Director of the United States Patent and Trademark Office*